United States Patent [19]

Grinnell

[11] Patent Number: 5,496,851

[45] Date of Patent: Mar. 5, 1996

[54] METHODS OF INHIBITING CELL-CELL ADHESION

[75] Inventor: Brian W. Grinnell, Indianapolis, Ind.

[73] Assignee: Eli Lilly and Company, Indianapolis, Ind.

[21] Appl. No.: 422,295

[22] Filed: Apr. 14, 1995

Related U.S. Application Data

[62] Division of Ser. No. 385,934, Feb. 9, 1995.

[51] Int. Cl.$^6$ ............................................. A61K 31/38
[52] U.S. Cl. ............................................................ 514/443
[58] Field of Search ............................................. 514/443

[56] References Cited

U.S. PATENT DOCUMENTS

| | | | |
|---|---|---|---|
| 4,133,814 | 1/1979 | Jones et al. | 546/202 |
| 4,380,635 | 4/1983 | Peters | 546/202 |
| 4,418,068 | 11/1983 | Jones | 424/267 |

FOREIGN PATENT DOCUMENTS

| | | |
|---|---|---|
| WO93/10113 | 5/1993 | Japan . |
| WO93/1074 | 6/1993 | WIPO . |

OTHER PUBLICATIONS

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.
Evans et al., "Raloxifene is a Tissue Specific Estrogen Agonist", Am Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Glasebrook et al., "Multiple Binding Sites for the Anti–estrogen Raloxifene", Am Soc. Bone & Min. Res., Tampa, Sep. 18–22, 1993.
Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.
Sato et al., "DEXA Analysis of Raloxifene Effects on the Bones From Ovariectomized Rats", Am. Soc. for Bone and Min. Res., Tampa, Sep. 18–22, 1993.
Yang et al., "Raloxifene an Anti–Estrogen, Simulates the Effects of Estrogen in Inhibiting Bone Resorption Through Regulating TGFB–3 Expression in Bone;" Am. Soc. for Bone and Min. Res., Tampa, Sep. 18–22, 1993.
Black et al., "Distinct, Structure–Related Profiles of Estrogenic and Anti–Estrogenic Activity in the Tamoxifen and LY117018 Series;" The Endocrine Society, Abstract 1982.
Black et al., "Uterine Bioassay of Tamoxifen, Trioxifene, and New Estrogen Antagonist (LY117018) in Rats and Mice," Life Sciences, 26:1980, 1453–1458.
Black et al., "Differential Interaction of Antiestrogens with Cytosol Estrogen Receptors," Molecular and Cellular Endocrinology, 22:1981, 95–103.
Black et al., "Evidence for Biological Action of the Antiestrogens LY117018 and Tamoxifen by Different Mechanisms," Endocrinology 109;1981, 987–989.
Black L. J. "Biological Actions and Binding Properites of a New Estrogen Antagosist LY117018," In: Homone Antagonists, 129–82, 1982 (M. K. Agarwal ed.) Walter de Gruyter and Co., Berlin New York.
Black et al., LY156758: A Unique Antiestrogen Displaying High Affinity for Estrogen Receptors, Negligible Estrogenic Activity and Near–Total Estrogen Antagonism in Vivo. Presented at the Fifth Annual San Antonio Breast Cancer Synposium, San Antonio, Texas, Nov. 5–6, 1982.
Black et al., The Antiestrogenic Action of LY139481: Species Uniformity Duration of Action and Kinetics of 3H–LY139481 Distribution in Vivo. Sixty–fifth Annual Meeting of the Endocrine Society, San Antonio, Texas, Jun. 8–10, 1983, abs. 93.
Black et al., Antagonism of Estrogen Action with a New benzothiophene Derived Antiestrogen, Life Sciences, 32:1983. 1031–1036.
Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.
Black et al., Synthesis and Antiestrongenic Activity of [3,4–Dihydro–2(4–methoxyhpheny)–1–napthalenyl][4–[2–pyrrolidinyl) ethoxyl]–phenyl]methanone, methanesulfonic acid salt, Journal of Medicinal Chemistry 22;1979, 962–966.
Black et al., Antiestrogens 2. Structure Activity Studies in a Series of 3–Aroyl–2–arylbenzo[b]thiophene Derivatives Leading to [6–Hydroxy–2–(4–hydroxyphenyl)benzo[b]thien–3–yl][4–[2–(1–piperidinyl)ethoxy]–phenyl] methanone Hydrochloride (LY156758), a Remarkably Effective Estrogen Antagonist with Only Minimal Intrinsic Estrogenicity, J. Med. Chem. 27(8), 1984, 1057–1066.

*Primary Examiner*—T. J. Criares
*Attorney, Agent, or Firm*—James J. Sales

[57] ABSTRACT

A method of inhibiting cell-cell adhesion comprising administering to a human in need thereof an effective amount of a compound having the formula

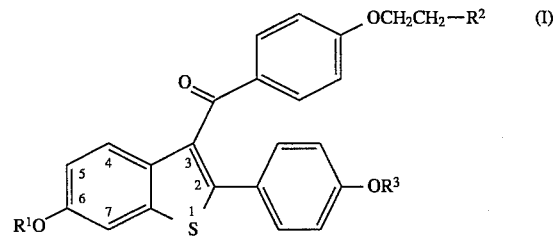

wherein $R^1$ and $R^3$ are independently hydrogen,

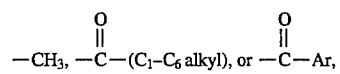

wherein Ar is optionally substituted phenyl;
$R^2$ is selected from the group consisting of pyrrolidine, hexamethyleneamino, and piperidino; or a pharmaceutically acceptable salt of solvate thereof.

3 Claims, No Drawings

METHODS OF INHIBITING CELL-CELL ADHESION

This application is a division of application Ser. No. 08/385,934, filed Feb. 9, 1995, now pending.

BACKGROUND OF THE INVENTION

The vascular endothelium constitutes a major organ that functions as a regulator of blood coagulation, inflammation and in the exchange of fluids and mediators between the intravascular compartment and parenchyma tissues. As such, the proper function of the endothelium is critical to overall homeostasis. A dysfunction of the endothelium resulting from an alteration in the expression of important surface molecules, can result in coagulation defects, local and systemic vascular inflammation, and enhancement in the progression and rupture of atherosclerotic plaque. These effects can further result in conditions including myocardial infarction, deep venous thrombosis, disseminated intravascular thrombosis, and stroke.

Certain cell surface proteins are altered in response to a vascular injury or insult, and can be used as markers of a dysfunctional endothelium. A critical class of such proteins is the receptors/ligands mediating cell-cell adhesion, including the integrins, selectins (e.g. ELAM) and members of the immunoglobulin superfamily such as ICAM and VCAM. These molecules are increased in response to a variety of stimuli including cytokines, and in addition to being important markers of a dysfunctional endothelium, play a key role in thrombotic, inflammatory and atherogenic processes in the vascular wall. Other activities, such as surface anticoagulant responses, are also impaired in states of endothelial dysfunction, A compound that could block endothelial dysfunction, as determined by measuring it ability to inhibit cell-cell adhesion or expression of procoagulant activities, could be useful in treating conditions such as sepsis, injuries involving major tissue damage and trauma, systemic inflammatory response syndrome, sepsis syndrome, septic shock and multiple organ dysfunction syndrome including DIC as well as atherosclerotic plaque rupture and its associated sequela. Because cell-cell adhesion is a fundamental process of broad biological importance, the ability to specifically modulate adhesive proteins has the potential for many clinical applications outside of the vascular tissue including its use as an anti-inflammatory agent.

SUMMARY OF THE INVENTION

This invention provides methods for inhibiting cell-cell adhesion comprising administering to a human need thereof an effective amount of a compound of formula I

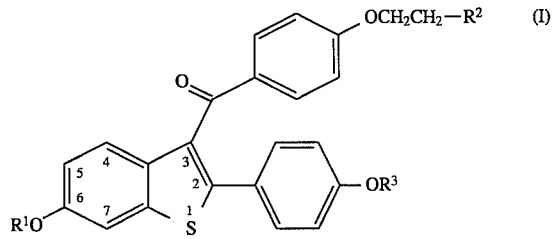

wherein $R^1$ and $R^3$ are independently hydrogen,

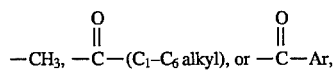

wherein Ar is optionally substituted phenyl;

$R^2$ is selected from the group consisting of pyrrolidino, hexamethyleneimino, and piperidino; and pharmaceutically acceptable salts and solvates thereof.

DETAILED DESCRIPTION OF THE INVENTION

The current invention concerns the discovery that a select group of 2-phenyl-3-aroylbenzothiophenes (benzothiophenes), those of formula I, are useful for inhibiting cell-cell adhesion, and particularly, vascular cell-cell adhesion. Also, the compounds are useful for inhibiting vascular endothelium dysfunction.

The methods of use provided by this invention are practiced by administering to a human in need thereof a dose of a compound of formula I or a pharmaceutically acceptable salt or solvate thereof, that is effective to inhibit cell-cell adhesion or its effects. The term "inhibit" includes its generally accepted meaning which includes prohibiting, preventing, restraining, and slowing, stopping or reversing. As such, the present method includes both medical therapeutic and/or prophylactic administration, as appropriate.

Raloxifene, a compound of this invention wherein it is the hydrochloride salt of a compound of formula 1, $R^1$ and $R^3$ are hydrogen and $R^2$ is 1-piperidinyl, is a nuclear regulatory molecule. Raloxifene has been shown to bind to the estrogen receptor and was originally thought to be a molecule whose function and pharmacology was that of an anti-estrogen in that it blocked the ability of estrogen to activate uterine tissue and estrogen dependent breast cancers. Indeed, raloxifene does block the action of estrogen in some cells; however in other cell types, raloxifene activates the same genes as estrogen does and displays the same pharmacology, e.g., osteoporosis, hyperlipidemia. As a result, raloxifene has been referred to as an anti-estrogen with mixed agonist-antagonist properties. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, acylated, and deprotected to form the formula I compounds. Examples of the preparation of such compounds are provided in the U.S. patents discussed above. Optionally substituted phenyl includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means, Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit cell-cell adhesion or its effects, or any other use disclosed herein, and according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed to effectively inhibit cell-cell adhesion or its effects, or any other use disclosed herein.

It is usually preferred to administer a compound of formula I in the form of an acid addition salt, as is customary in the administration of pharmaceuticals bearing a basic group, such as the piperidino ring. It is also advantageous to administer such a compound by the oral route. For such purposes the following oral dosage forms are available.

Formulations

In the formulations which follow, "Active ingredient" means a compound of formula I.

Formulation 1: Gelatin Capsules

Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

Formulation 2: Raloxifene capsule

| Ingredient | Quantity (mg/capsule) |
|---|---|
| Raloxifene | 1 |
| Starch, NF | 112 |
| Starch flowable powder | 225.3 |
| Silicone fluid 350 centistokes | 1.7 |

Formulation 3: Raloxifene capsule

| Ingredient | Quantity (mg/capsule) |
|---|---|
| Raloxifene | 5 |
| Starch, NF | 108 |
| Starch flowable powder | 225.3 |
| Silicone fluid 350 centistokes | 1.7 |

Formulation 4: Raloxifene capsule

| Ingredient | Quantity (mg/capsule) |
| --- | --- |
| Raloxifene | 10 |
| Starch, NF | 103 |
| Starch flowable powder | 225.3 |
| Silicone fluid 350 centistokes | 1.7 |

Formulation 5: Raloxifene capsule

| Ingredient | Quantity (mg/capsule) |
| --- | --- |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.
A tablet formulation is prepared using the ingredients below:
Formulation 6: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.
Alternatively, tablets each containing 0.1–1000 mg of active ingredient are made up as follows:
Formulation 7: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.
Suspensions each containing 0.1–1000 mg of medicament per 5 mL dose are made as follows:
Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

In vitro Cell Adhesion Assays

Human Umbilical Vein Endothelium Cells (HUVEC) or Human Aortic Endothelium (HAE) were obtained from Clonetics (San Diego) and grown in the EBM medium supplied by Clonetics. Cells were plated in 96 well plates at a density to obtain confluent monolayers following overnight incubation at 37 degrees C. Test compound was added and incubated in serum-free medium for 8–20 hours. Monolayers were then incubated with or without 2 ng/ml IL-1 or with 20 nanograms Tumor Necrosis Factor (TNF) for 4 to 24 hours prior to the binding assay in a total volume of 75 to 100 microliters in the presence of the test compound. Following incubations, tritium-labelled U937 cells were added in 50 microliter volumes at from 1 to 3×10 (6) cells per well. The U937 cells were tritium labelled by the addition of 3H-thymidine to a final concentration of 1 microcurie per milliliter, followed by 18 to 20 hours incubation. Cells were washed with PBS prior to use to remove excess label. After a 20 minute incubation of the labeled U937 cells with the endothelial cells, the wells were aspirated and washed four times with calcium-containing PBS. The monolayer and adherent U937 cells were solubilized by the addition of 0.25% SDS/0.1N NaOH for 5 minutes with agitation. The level of binding was determined by scintillation counting of the solubilized cells.

Anticoagulant activity assay

Confluent cultures of IL1-treated (2 ng/ml) or untreated human endothelial cells in 96 well plates were washed once with HBSS to remove serum proteins and incubated with serum-free medium (DMEM/F-12 medium, 20 mM-HEPES, pH 7.5, 50 mg/ml gentamicin, 1 mg/ml human transferrin and 1 mg/ml bovine insulin. ) containing 400 nM-recombinant human protein C and 10 nM human thrombin, Cells were incubated at 37° C., and at various times medium was removed and added to an equal volume of a solution of 20 mM Tris-HCl pH 7.5, 150 mM NaCl, 1 mg/ml BSA and 10 U/ml Hirudin. The samples were incubated in the hirudin-contain buffer for 5 min to inhibit thrombin activity. The amount of activated protein C generated was determined by the addition of chromogenic substrate (S-2366) to a final concentration of 0.75 mM, and measuring the change in absorbance units/minute at 405 nm in a ThermoMax kinetic micro-titer plate reader (Molecular Devices). In all experiments, samples of the protein C/thrombin solution were incubated in wells without cells to determine basal levels of thrombin-catalyzed activation of protein C. The amount of activated protein C generated is expressed as the absorbance (mOD) per minute per microgram of cellular protein.

Results

Human umbilical vein endothelial cells (HUVEC) were treated with compound A where $R^1$ and $R^3$ are hydrogen and $R^3$ is pyrrolidino, concurrent to the induction of adhesion molecule expression by TNF. As shown in Table I, the presence of 100 nM of compound A resulted in an approximate 40% reduction in the level of cell-cell adhesion in this assay. When cells were pretreated with only 10 nM of compound A for approximately 20 hours before induction with TNF, an approximate 65 % reduction in adhesion was observed (Table 2). We also treated both HUVECs and human aortic endothelial cells (HAEC) with IL1, another inflammatory mediator to induce adhesion molecule expression in the presence of 10nM compound A. As shown in Table 3, compound A effectively inhibited the IL1-induction of adhesion in both cell lines. Thus compound A can block the induction of adhesion molecule expression mediated by two independent means and in both venous and arterial cells.

As further evidence for the ability of this compound to modulate the functional properties of the endothelium, we measured the ability of the endothelial cells to activate human protein C, a natural regulatory function that is down regulated during states of endothelial dysfunction. As shown in Table 4, IL1 treatment of the cells significantly reduced the capability of the endothelium to support protein C generation. However, following treatment of the cells with compound A, the suppression of this function by IL1 was essentially eliminated. The above data indicate that compound A protects the cells from activation of inflammatory and procoagulant activities.

TABLE 1

Effect of Compound A on adhesion of U937 cells to TNF-activated human umbilical vein endothelial cells (HUVEC)

| Condition | Percent Binding Activity[a] |
|---|---|
| Untreated control | 0 ± 7.5 |
| TNF treated | 100 ± 9.5 |
| TNF plus compound A (100 nM) | 62 ± 17 |

[a]The level of binding is expressed as the percent of the number of U937 cells bound to the endothelium before and after TNF induction.

TABLE 2

Effect of pretreatment with compound A on adhesion of U937 cells to TNF-activated human umbilical vein endothelial cells (HUVEC)

| Condition | Percent Binding Activity[a] |
|---|---|
| Untreated control | 0 ± 20 |
| TNF treated | 100 ± 16 |
| TNF plus compound A (10 nM) | 34 ± 8 |

[a]The level of binding is expressed as the percent of the number of U937 cells bound to the endothelium before and after TNF induction.

TABLE 3

Effect of pretreatment with compound A on adhesion of U937 cells to IL1-activated human aortic endothelial cells (HAEC) and human umbilical vein endothelial cells (HUVEC)

| Condition | Percent Binding Activity[a] to HUVEC | HAEC |
|---|---|---|
| IL1-treated | 100 ± 14 | 100 ± 8 |
| IL1 plus compound A (10 nM) | 18 ± 13 | 54 ± 7 |

TABLE 3-continued

Effect of pretreatment with compound A on adhesion of U937 cells to IL1-activated human aortic endothelial cells (HAEC) and human umbilical vein endothelial cells (HUVEC)

| Condition | Percent Binding Activity[a] to HUVEC | HAEC |
|---|---|---|

[a]The level of binding is expressed as the percent of the number of U937 cells bound to the endothelium before and after IL1 induction.

TABLE 4

Effect of compound A on thrombin-catalyzed activation of human protein C on endothelial cells treated with IL-1

| Condition | Level of protein C produced (mOD/min/ug) |
|---|---|
| untreated control | 8.8 ± 1.4 |
| IL1-treated | 3.7 ± 0.4 |
| IL1 plus compound A | 7.6 ± .6 |

I claim:

1. A method to inhibit inflammatory and disrupted normal coagulation process in patients with disorders of the vascular endothelium comprising administering to a patent in need thereof an effective amount of a compound having the formula

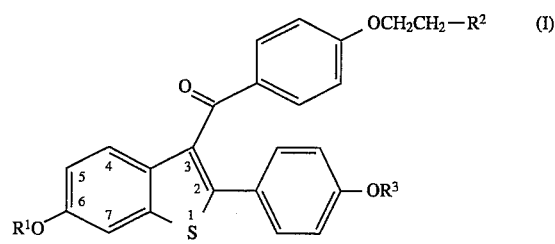

wherein $R^1$ and $R^3$ are independently hydrogen,

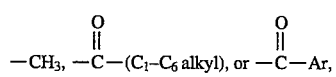

wherein Ar is optionally substituted phenyl;

$R^2$ is selected from the group consisting of pyrrolidine, hexamethylenemino, and piperidino; or a pharmaceutically acceptable salt of solvate thereof.

2. The method of claim 1 wherein said compound is the hydrochloride salt thereof.

3. The method of claim 1 wherein said compound is

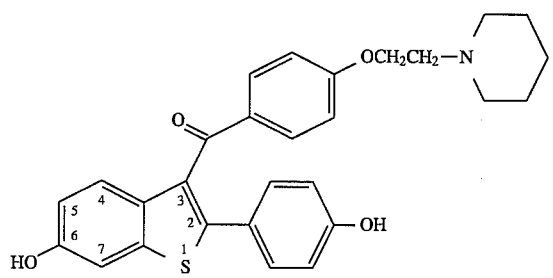

or its hydrochloride salt.

* * * * *